US011393336B2

(12) United States Patent
Szczepanik et al.

(10) Patent No.: US 11,393,336 B2
(45) Date of Patent: Jul. 19, 2022

(54) SMOG ANALYSIS VIA DIGITAL COMPUTING PLATFORMS (71) Applicant: International Business Machines Corporation, Armonk, NY (US)

(72) Inventors: Grzegorz Piotr Szczepanik, Kracow (PL); Kushal S. Patel, Pune (IN); Lukasz Jakub Palus, Kracow (PL); Sarvesh S. Patel, Pune (IN)

(73) Assignee: International Business Machines Corporation, Armonk, NY (US)

( * ) Notice: Subject to any disclaimer, the term of this patent is extended or adjusted under 35 U.S.C. 154(b) by 106 days.

(21) Appl. No.: 16/988,997

(22) Filed: Aug. 10, 2020

(65) Prior Publication Data
US 2022/0044561 A1 Feb. 10, 2022

(51) Int. Cl.
| G08G 1/01 | (2006.01) |
| G08G 1/048 | (2006.01) |
| H04W 4/40 | (2018.01) |
| G01D 21/02 | (2006.01) |
| G01S 19/01 | (2010.01) |

(52) U.S. Cl.
CPC ............ *G08G 1/048* (2013.01); *G01D 21/02* (2013.01); *G01S 19/01* (2013.01); *H04W 4/40* (2018.02)

(58) Field of Classification Search
CPC ......... G08G 1/048; H04W 4/40; G01D 21/02; G01S 19/01
USPC ....................................................... 340/939
See application file for complete search history.

(56) References Cited

U.S. PATENT DOCUMENTS

| 5,532,690 A | 7/1996 | Hertel |
| 8,818,725 B2 | 8/2014 | Ricci |
| 10,838,931 B1* | 11/2020 | Spiegel ............... G06F 16/2228 |
| 10,909,839 B1* | 2/2021 | Kursar ................. G08B 25/016 |
| 2005/0137763 A1* | 6/2005 | Watkins ............... G07C 5/0841 |
| | | 701/29.5 |

(Continued)

FOREIGN PATENT DOCUMENTS

| CN | 201000431 Y | 1/2008 |
| CN | 204109933 U | 1/2015 |

(Continued)

OTHER PUBLICATIONS

"Patent Cooperation Treaty PCT Notification of Transmittal of the International Search Report and the Written Opinion of the International Searching Authority, or the Declaration", Applicant's file reference P201904859PCT01, International Application No. PCT/IB2021/056850, International Filing Date Jul. 28, 2021, dated Nov. 11, 2021, 9 Pgs.

(Continued)

*Primary Examiner* — Kerri L McNally
*Assistant Examiner* — Thang D Tran
(74) *Attorney, Agent, or Firm* — Alexander G. Jochym (57) ABSTRACT

Disclosed is a system, computer program product and computer-implemented method for smog analysis which provides sending a data collection signal to one or more vehicles including one or more sensors via a base station, receiving data from the one or more vehicles, including sensor data, analyzing the received data for determining a smog status, and sending traffic information to a plurality of vehicles. The traffic information may include the determined smog status and the plurality of vehicles may include the one or more vehicles.

20 Claims, 5 Drawing Sheets

(56) References Cited

U.S. PATENT DOCUMENTS

| | | | |
|---|---|---|---|
| 2005/0143096 A1 | 6/2005 | Boesch | |
| 2010/0148974 A1* | 6/2010 | Yang | G08B 17/125 |
| | | | 340/628 |
| 2010/0331023 A1 | 12/2010 | Cai | |
| 2011/0155397 A1* | 6/2011 | Icove | G08B 17/12 |
| | | | 169/16 |
| 2012/0190386 A1* | 7/2012 | Anderson | H04L 67/306 |
| | | | 455/456.3 |
| 2014/0324275 A1* | 10/2014 | Stanek | G07C 5/008 |
| | | | 701/31.4 |
| 2016/0061625 A1* | 3/2016 | Wang | G01C 21/3691 |
| | | | 701/454 |
| 2016/0125307 A1* | 5/2016 | Zheng | G06N 20/00 |
| | | | 706/12 |
| 2016/0318368 A1* | 11/2016 | Alger | G01C 21/3453 |
| 2017/0032661 A1* | 2/2017 | Moffa | G08B 29/145 |
| 2017/0076509 A1* | 3/2017 | Scofield | A61B 5/02055 |
| 2017/0107436 A1* | 4/2017 | Agarwal | C10L 1/14 |
| 2017/0134653 A1* | 5/2017 | Gettings | G08B 13/19695 |
| 2017/0270375 A1* | 9/2017 | Grauer | G06K 9/6293 |
| 2018/0268473 A1* | 9/2018 | Um | G06Q 30/0645 |
| 2018/0268621 A1* | 9/2018 | Oz | G06Q 30/0278 |
| 2018/0305876 A1* | 10/2018 | Langford | G08G 1/0145 |
| 2019/0084369 A1* | 3/2019 | Duan | B60H 1/00771 |
| 2019/0121782 A1* | 4/2019 | Sun | G01D 18/008 |
| 2019/0272755 A1* | 9/2019 | Giorgi | H04W 4/40 |
| 2019/0308487 A1* | 10/2019 | Badger, II | B60H 1/00821 |
| 2019/0394720 A1* | 12/2019 | McCoy | H04W 4/80 |
| 2020/0062074 A1* | 2/2020 | Macneille | B60H 1/00971 |
| 2020/0068455 A1* | 2/2020 | Badic | H04W 4/029 |
| 2020/0090510 A1* | 3/2020 | Nagarajan | G08G 1/096775 |
| 2020/0120064 A1* | 4/2020 | Cho | H04L 61/2007 |
| 2020/0231121 A1 | 7/2020 | Dudekula | |
| 2020/0355508 A1* | 11/2020 | Bruns | G01C 21/3461 |
| 2021/0116913 A1* | 4/2021 | Dingli | G05D 1/0214 |
| 2021/0150386 A1* | 5/2021 | DeLuca | G06N 5/04 |
| 2021/0160849 A1* | 5/2021 | Sun | H04W 72/046 |
| 2021/0242960 A1* | 8/2021 | Li | H04L 1/0003 |

FOREIGN PATENT DOCUMENTS

| | | |
|---|---|---|
| CN | 204759452 U | 11/2015 |
| CN | 107221152 A | 9/2017 |
| CN | 208092894 U | 11/2018 |
| CN | 109658662 A | 4/2019 |
| CN | 106845371 B | 10/2019 |
| CN | 110874929 A | 3/2020 |
| EP | 3217400 B1 | 11/2018 |
| WO | 2012083780 A1 | 6/2012 |

OTHER PUBLICATIONS

"European Parliament Committee on Budgetary Control", Wikipedia, This page was last edited on Dec. 12, 2019, 3 pages, <https://en.wikipedia.org/wiki/European_Parliament_Committee_on_Budgetary_Control>.

"Watson Speech to Text", IBM, Printed Apr. 1, 2020, 4 pages, <https://www.ibm.com/in-en/cloud/watson-speech-to-text>.

Popeanga et al., "Real-Time Business Intelligence for the Utilities Industry", Database Systems Journal vol. III, No. Jan. 2012, 10 pages.

Chen et al., "Smog Disaster Forecasting using Social Web Data and Physical Sensor Data", 2015 IEEE International Conference on Big Data, ©2015 IEEE, 8 pages.

* cited by examiner

SMOG ANALYSIS VIA DIGITAL COMPUTING PLATFORMS

FIELD OF THE INVENTION

Certain embodiments of the invention relate to the field of digital computer systems and methods. More specifically, certain embodiments of the invention relate to systems and methods for smog analysis via digital computing platforms.

BACKGROUND OF THE INVENTION

Smog is a type of air pollutant. The word "smog" is a portmanteau of the words smoke and fog to refer to smoky fog, its opacity, and odor. It is usually vey highly toxic to humans and can cause severe sickness, shortened life, or death. Smog also affects visibility and thus impacts vehicular networks, such as traffic flow and vehicular mobility. Furthermore, people have different sensitivity levels to smog, with some reacting so adversely as to impair current activities, such as driving or working outside.

There are multiple factors, both direct and indirect, that drive smog intensity and the problems associated with it. As smog generation is dependent on various components, it is often difficult to analyze and predict accurately. However, advancements in telecommunications and computing infrastructures may be used to advance smog analysis, prediction, and information transfer.

BRIEF SUMMARY OF THE INVENTION

Various embodiments provide a system and method of smog analysis as described by the subject matter of the independent claims. Advantageous embodiments are described in the dependent claims. Embodiments of the present invention can be freely combined with each other if they are not mutually exclusive.

In one aspect, the invention relates to a computer-implemented method for smog analysis. The computer-implemented method includes sending a data collection signal to one or more vehicles via a base station, where each vehicle includes one or more sensors, receiving data from the one or more vehicles, where the data includes sensor data collected by the one or more sensors of the one or more vehicles, analyzing the received data for determining a smog status, and sending traffic information to a plurality of vehicles. The traffic information may include the determined smog status and the plurality of vehicles may include the one or more vehicles.

In another aspect, the invention relates to a system for smog analysis, the system including a 5G cellular network configured to send a data collection signal to one or more vehicles via a base station, where each vehicle includes one or more sensors, receive data from the one or more vehicles, where data includes sensor data collected by the one or more sensors of the one or more vehicles, analyze the received data for determining a smog status, and send traffic information to a plurality of vehicles. The traffic information may include the determined smog status and the plurality of vehicles may include the one or more vehicles.

In another aspect, the invention relates to a system for smog analysis, the system including a cellular network including a base station and a core, the core configured to send a data collection signal to one or more vehicles via the base station, where each vehicle includes one or more sensors, receive data from the one or more vehicles, where data includes sensor data collected by the one or more sensors of the one or more vehicles, analyze the received data for determining a smog status, and send traffic information to a plurality of vehicles via the base station. The traffic information includes the determined smog status and the plurality of vehicles includes the one or more vehicles.

These features may have the advantages of dynamically updating smog status and smog forecasts quickly and accurately using data collected by multiple mobile sensors. The features may also have the advantages of distributing the analysis over one or more resources (e.g., servers) of a network, thereby providing a more efficient and time sensitive manner of sharing the workload, and particularly utilizing the more advanced communication infrastructure of cellular networks, such as 5G networks, as well as other standardized cellular networks.

BRIEF DESCRIPTION OF SEVERAL VIEWS OF THE DRAWINGS

The following embodiments of the invention are explained in greater detail, by way of example only, making reference to the drawings in which.

DETAILED DESCRIPTION OF THE INVENTION

The descriptions of the various embodiments of the present invention have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

According to embodiments, a network implemented system, computer program product and computer-implemented method for smog analysis includes sending a data collection signal to one or more vehicles via a base station, where each vehicle includes one or more sensors, receiving data from the one or more vehicles, the data including sensor data collected by the one or more sensors of the one or more vehicles, analyzing the received data for determining a smog status, and sending traffic information to a plurality of vehicles, where the traffic information may include the determined smog status and the plurality of vehicles may include the one or more vehicles. These features may have the advantages of dynamically updating smog status and smog forecasts quickly and accurately using data collected by multiple mobile sensors. The features may also have the advantages of distributing the analysis over one or more resources (e.g., servers) of a network, thereby providing a more efficient and time sensitive manner of sharing the workload, and particularly utilizing the more advanced communication infrastructure of cellular networks, such as 5G networks, as well as other standardized cellular networks.

According to one embodiment, a bounded area of land is defined. The coverage area of the base station includes at least a portion of the bounded area of land, and the data collection signal includes geographic data defining boundaries of the bounded area of land. Data is received from only a subset of the one or more vehicles located within the bounded area of land. These features may have the advantages of defining in real-time bounded land areas that may include portions of one or more cellular coverage areas, including entire cellular coverage areas, in which smog status and prediction is particularly useful and/or needed.

According to one embodiment, upon receiving the data collection signal, each vehicle of the one or more vehicles compares current GPS coordinates obtained from a sensor with the received geographic data for determining if the vehicle is within the bounded land area. The vehicle collects data by the one or more sensors only if the vehicle is determined to be within the bounded land area. These features may have the advantages of limiting the volume of data collected, thus dedicating limited computing resources to analyzing smog status and generating smog forecasts in conjunction with targeted data for the specifically defined bounded land areas.

According to one embodiment, a frequency of sending the data collection signal is determined, based on the data received. The data collection signal may then be sent to the one or more vehicles at the determined frequency. These features may have the advantages of tuning the system to collect more or less data based upon current conditions, thereby providing more accurate analyses of smog conditions and/or more accurate smog forecasts and/or optimizing the use of the resources of the system and method of smog analysis.

According to one embodiment, external data is received from internet services and/or databases. The external data may include one or more of weather data, weight of the one or more vehicles, engine-maintenance history of the one or more vehicles, accident history of the one or more vehicles, PUC data of the one or more vehicles. The data received from the one or more vehicles and the data received from external sources may then be used for determining the smog status and/or forecasting smog. These features may have the advantages of using not only data collected by mobile in-field sensors but utilizing data from other Web-based sources and/or databases to augment the in-field sensor data to more accurately determine smog status/prediction.

According to one embodiment, the traffic information may include one or more of alternative route information, smog status of other predefined bounded areas of land and smog status forecasts for the predefined bounded area of land and the other predefined bounded areas of land. These features may have the advantages of providing to the traveling public other routes to their destinations that avoid smoggy regions or regions that are forecasted to be smoggy and/or enable the public to make their own route adjustments based on the information received.

Figure 1:
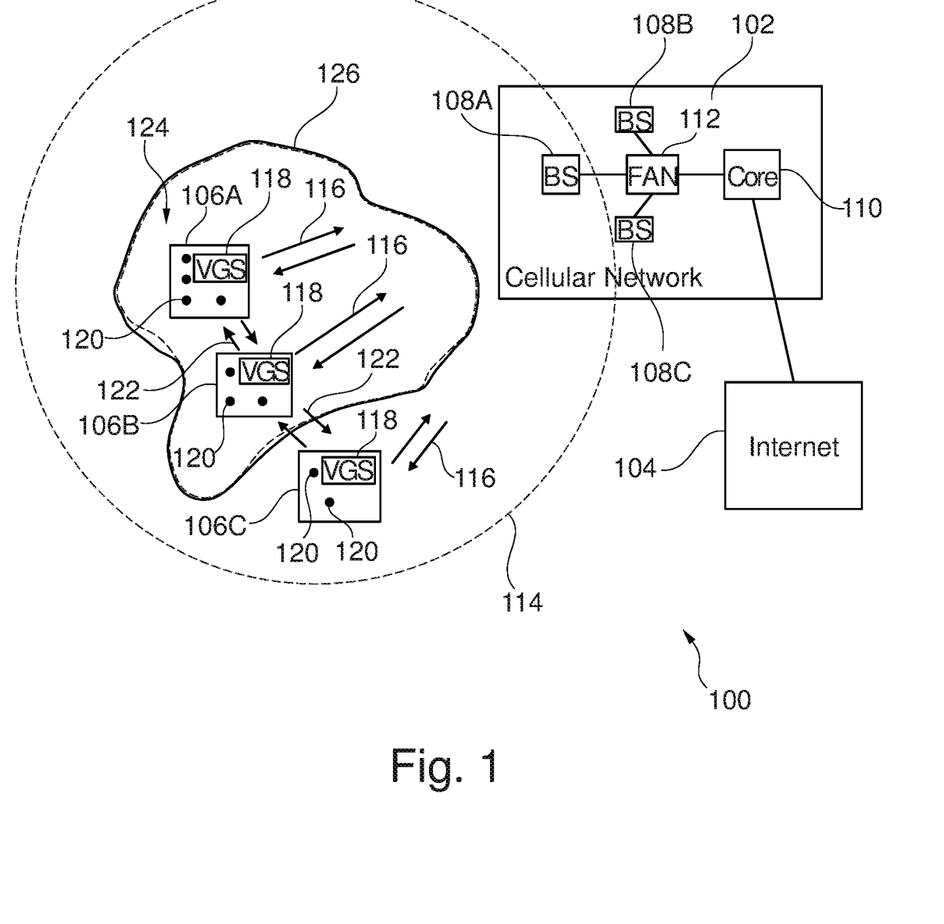
FIG. 1 is a schematic diagram of a system of communication networks, according to an embodiment of the present disclosure.

FIG. 1 is a schematic diagram of a system of communication networks 100, according to an embodiment of the present disclosure. The system of communication networks 100 includes a cellular network 102, the Internet 104, and one or more vehicles 106. In one embodiment, the cellular network may be a 5G cellular network, however, the scope of the present disclosure covers all types of cellular networks, such as 4G networks and networks utilizing GSM technology and networks utilizing CDMA technology.

The cellular network 102 includes at least one base station (BS) 108 and a core 110. In one embodiment, the base stations 108 are communicatively coupled to the core via a fixed access network (FAN) 112. As illustrated, the base station 108A includes a coverage area 114 (also referred to as a cell). The cellular network 102 and the vehicles 106 located within the coverage area 114 communicate with each other via wireless communications 116 and an antenna (not shown) associated with the base station 108A. The base stations 108B and 108C have corresponding coverage areas (not shown), thereby enabling other vehicles located in the corresponding coverage areas to communicate with the cellular network 102.

In on embodiment of the present disclosure, the core 110 is configured to send a data collection signal via the wireless communications 116 to the one or more vehicles 106 located within the coverage area 114 via the base station 108A. Some of the vehicles 106 may be equipped with a vehicle control system (VCS) 118 and one or more sensors 120, e.g., vehicles 106A, 106B and 106C. The vehicle control system 118 is a well-known component of many modern-day vehicles.

Figure 2:
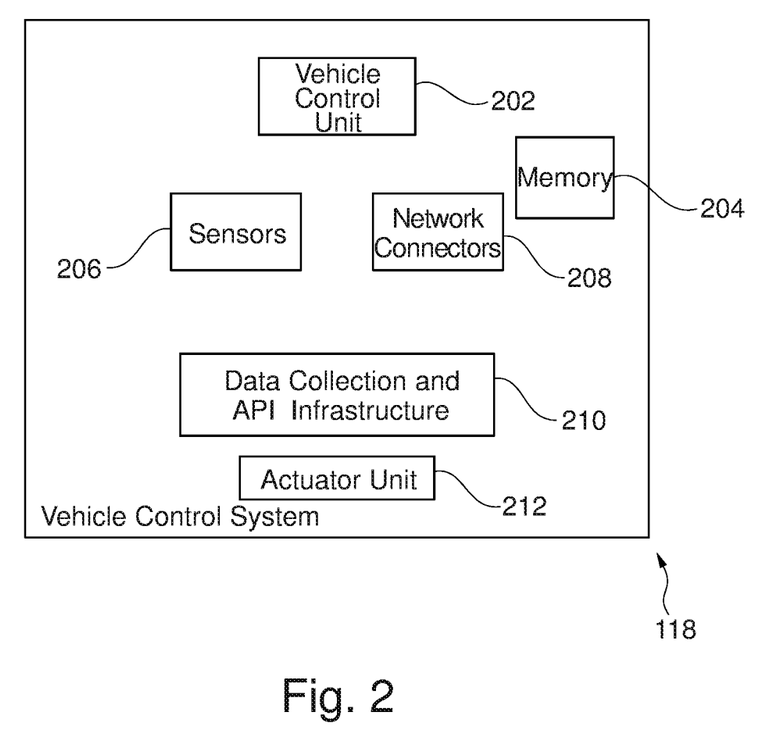
FIG. 2 is a schematic diagram of a vehicle control system, according to an embodiment of the present disclosure.

FIG. 2 is a schematic diagram of a vehicle control system 118, according to an embodiment of the present disclosure. The vehicle control system 118 may include a vehicle control unit 202 (e.g., processors and/or microcontrollers), memory 204, device drivers for the sensors 206, V2V and/or V2I network connectors 208, data collection and application programming interface (API) infrastructure (including API connectors) 210 and an actuator unit 212 having one or more actuators for activating/deactivating the sensors and/or orienting the sensors for collection of data. Vehicle control systems may operate in conjunction with networks, such as vehicle-to-vehicle (V2V) networks and/or vehicle-to-infrastructure (V2I) networks. As is well known, V2V and V2I networks enable communication (FIG. 1, 122) between vehicles and between vehicles and infrastructure for collision avoidance, braking, stability control and autonomous driving, for example. Data collection and the underlying API infrastructure of vehicle control systems are well known and will not be discussed in the present disclosure in further detail. The vehicle control system 118 may also include other logical layers that are well known in the operation of conventional vehicle control systems, include hardware, software and/or firmware elements for implementation.

Referring again to FIG. 1, and in one embodiment, the sensors 120 may include audio sensors, visual sensors, temperature sensors, engine-based sensors, emission sensors and/or GPS sensors. However, the scope of the present disclosure covers all types of sensors, including, for example, orientation sensors, accelerometers and sensors that detect and collect data of the vehicle environment.

In an embodiment, audio sensors 120 may be configured to receive speech or audio commands from an operator (i.e., driver) and/or passengers in the vehicle 106. For example, the driver may want to comment on traffic conditions, weather, accidents, average observed highway speed, parameters of the vehicle (such as make and model of the vehicle and/or weight of the vehicle), and ambient conditions, such as observable smog levels. In other embodiments, visual sensors 120 may be configured to capture the environment surrounding the vehicle, thereby sending visual data corresponding to traffic conditions, extent of vegetation coverage, weather, accidents and visible smog. The engine-based sensors 120, emission sensors 120 and GPS sensors 120 may capture (i.e. measure) speed of the vehicle 106, revolutions per second of the engine of the vehicle, oil temperature of the engine, water temperature of the engine, emissions data and location of the vehicle, for example. The sensors 120 may also be components of a V2V and/or V2I network, thereby capturing data corresponding to neighboring vehicles and/or infrastructure along the highway road. For example, the sensors 120 may provide data corresponding to neighboring vehicles not equipped to communicate with cellular networks, such as 5G cellular networks.

As referred to herein, all data retrieved, collected, and used, is used in an opt in manner, i.e., the data provider has gi'vvven permission for the data to be used. Any data or information used for which the provider has not opted in is data that is publicly available.

In one embodiment, the vehicle control system 118 receives a data collection signal from the cellular network 102. The data control signal may include instructions on which sensors to activate, the quantity of data to collect, sampling rates, and/or when to initiate and when to end the collection. In other embodiments, reception of the data collection signal merely triggers the vehicle control system 118 to actuate one or more of the sensors 120 to collect data. For example, each time a data collection signal is received by the vehicle control system 118, the system 118 initiates one or more of the sensors 120 to collect data at a predetermined sampling rate for a predetermined length of time as stored in the memory 204, or as communicated via the data control signal.

In another embodiment, the data collection signal may instruct the vehicle control system 118 to collect data from the memory 204, data such as engine-maintenance history of the vehicle 106, accident history of the vehicle 106 and pollution-under-control (PUC) data, if such data is stored in the memory 204. For the purposes of the present disclosure, data collected from the memory 204 by the vehicle control system will be considered to be data that may be received from the vehicle 106 by the cellular network 102.

In an embodiment of the present disclosure, the vehicle control system 118, upon collecting data from the sensors 120 and/or the memory 204, sends the data to the core 110 of the cellular network 102 via the base station 108A and the wireless communications 116.

As is common knowledge, base stations include antennas for transmitting and receiving signals (i.e., messages) to and from mobile units located in cells, such as the vehicles 106 equipped with the vehicle control systems 118 located in the cell 114 and configured to communicate with the cellular network 102. When mobile units leave a cell (e.g., cell 114) and enter an adjacent coverage area or adjacent cell, the mobile units are instructed by the wireless network 102 to switch (i.e., be handed over) to another base station (e.g., base station 108B) providing coverage for the adjacent cell.

Figure 3:
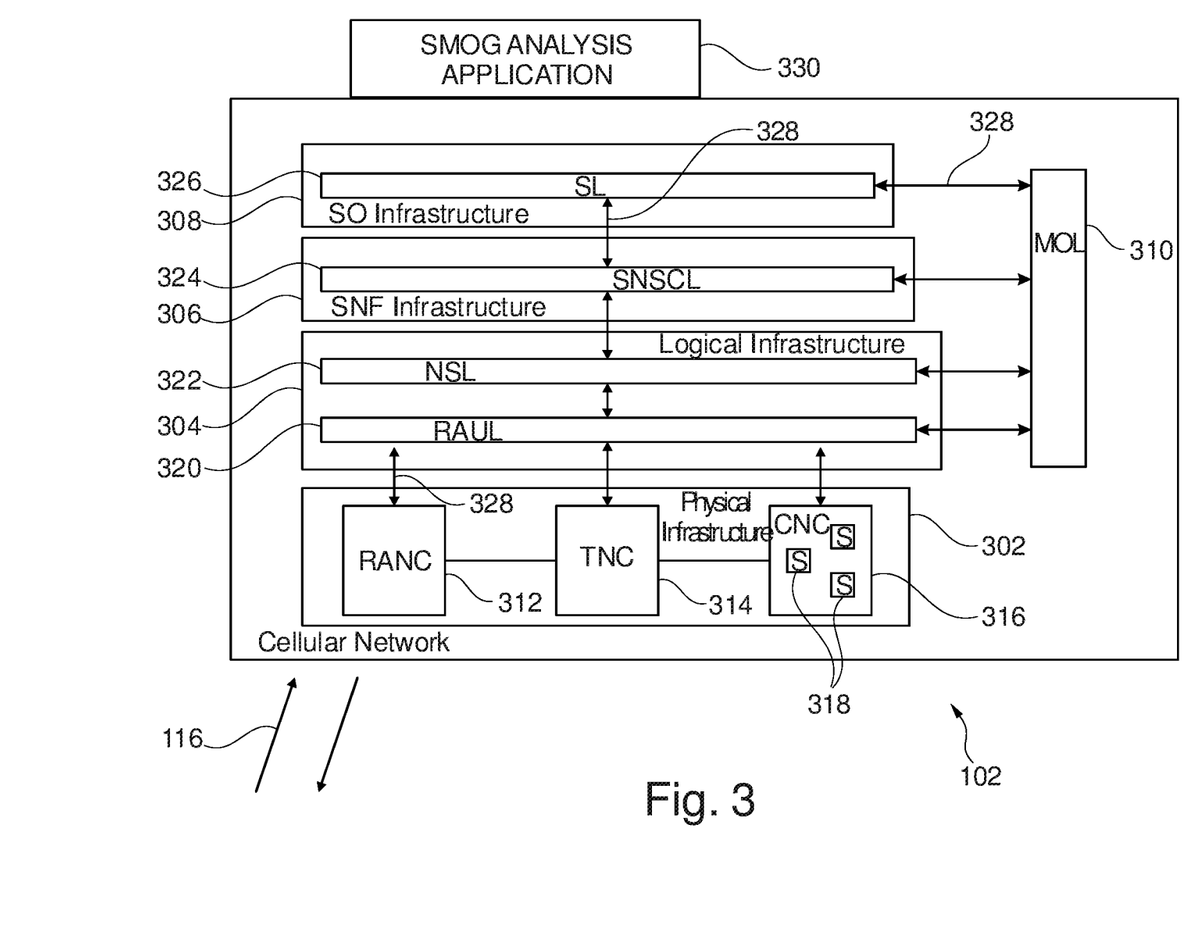
FIG. 3 is a schematic diagram of the cellular network of FIG. 1, according to an embodiment of the present disclosure.

FIG. 3 is a schematic diagram of the cellular network 102 of FIG. 1, according to an embodiment of the present disclosure.

The cellular network 102 includes a physical infrastructure 302, a logical infrastructure 304, a software network functions (SNF) infrastructure 306, a service orchestration (SO) infrastructure 308, and a management and orchestration layer (MOL) 310. The physical infrastructure includes a radio access network component (RANC) 312 (e.g., the one or more base stations 108 of FIG. 1), a transport network component (TNC) 314 (e.g., the fixed access network 112 of FIG. 1), and a core network component (CNC) 316 (e.g., core network 110 of FIG. 1). The core network 316 includes one or more servers (S) 318.

In some embodiments, the logical infrastructure 304 includes a resource abstraction and virtualization layer (RAVL) 320 and a networking slice layer (NSL) 322, the software network functions infrastructure 306 includes a software network service chain layer (SNSCL) 324, and the service orchestration infrastructure 308 includes a service layer (SL) 326. Communication between the different layers, and the resource abstraction and virtualization layer 320 and the components of the physical infrastructure 302 may be facilitated by application programming interfaces 328 (APIs). In one embodiment, the base stations 108 of the radio access network component 312 and the fixed access network 122 of the transport network component 314 include servers (not shown). In another embodiment of the present disclosure, the cellular network includes and/or is configured to execute, a smog analysis application 330 (i.e., a program). In one embodiment, the smog analysis application 330 includes computer programming instructions that when executed by the one or more servers 318, analyze the data received from the one or more vehicles 106 to determine a smog status of the coverage area 114 in which the vehicles are located. Environmental software and/or firmware applications are known in the art, and in one embodiment the scope of the present disclosure utilizes off-the-shell commercially available environmental analysis/forecast applications.

In one embodiment of the present disclosure, at least one server of the one or more servers 318 of the core component 316 (e.g., the core 110) is configured to receive the data from the one or more vehicles 106 via the base station 108A of the radio access network component 312 and the fixed access network 112 of the transport network component 314.

In an embodiment, the core 110 is configured to execute the smog analysis application 330 for processing the received data in a distributed manner over the one or more servers 318 utilizing network management architecture, such as the service layer 326, the software network service chain layer 324, the networking slice layer 322, the resource abstraction and virtualization layer 320, and the management and orchestration layer 310. In a further embodiment of the present disclosure, the execution of the smog analysis application is distributed over the one or more servers 318 utilizing the layers 310, 320, 322, 324 and 326 operating within the constraints and parameters of a 5G network management architecture.

In one embodiment, the resource abstraction and virtualization layer 320 is configured to receive the data via an API interface 328 from either the base station 312, the fixed access network 314, or a server of the one or more servers 318, and the management and orchestration layer 310 is configured to manage the distribution of tasks associated with execution of the smog analysis application 330 to the one or more servers 318 via the service layer 326, the software network service chain layer 324 and the networking slice layer 322.

Although in the embodiment described above, the cellular network includes smog analysis application 330, in the sense that the application 330 may reside on a server 318, in another embodiment, the smog analysis application resides on a server (not shown) external to the cellular network 102 and maintained by a third party vendor, for example.

In one embodiment, the core 316 (i.e., 110) is coupled to the Internet 104, as illustrated by FIG. 1. In a further embodiment, the core 316 is configured to receive external data from Web-based internet services and/or databases. For example, external data may include weather data, the weight of a vehicle, engine-maintenance history of a vehicle, accident history of a vehicle and PUC data of a vehicle. In one embodiment of the present disclosure, at least one server of the one or more servers 318 may be configured to receive the external data and the data from the one or more vehicles 106, and the core 316 may be configured to execute the smog analysis application in the distributed manner described above for processing (i.e., analyzing) the data from the one or more vehicles along with the external data to determine the smog status and/or a smog forecast.

For example, the smog analysis program may be configured to process the data (e.g., sensor data and data from memory) from the one or more vehicles, and in some embodiments, the external data to determine a smog status of the coverage area 114 in which the vehicles are presently located, as well as a smog forecast. Other external data may also be used for the smog forecast, such as traffic history within the coverage area or current environmental conditions, such as wind patterns, pressure systems, foliage coverage, local fires, etc. As an illustrative example, if an area has a traffic pattern that includes a high density of operating during daylight hours, which may even include a significant percentage of electric cars, but a low density of traffic operating during nighttime hours, which may even include a significant percentage of heavy diesel consumer vehicles, the smog analysis application may determine, based upon vehicle count, type of fuel, and perhaps other data as well, that the area is forecast to have a greater chance of smog during the daylight hours. Alternatively, and considering the above scenario, if the data received from the vehicles operating during nighttime hours show that some percentage of these vehicles are heavy weight older model tractor trailers with less engine maintenance and higher PUC scores, then the smog analysis application may determine a higher risk of smog during early evening and early evening morning times. In one embodiment, the smog analysis application processes the received vehicular data and/or external data, which indicate current vehicular status, vehicle history, and current and past traffic and environmental conditions, for determining smog levels and smog forecasts.

In another embodiment of the present disclosure, at least one server of the one or more servers 318 of the core 110 is configured to receive information that defines a bounded area of land, such as bounded area of land 124 (FIG. 1). For example, a maintenance operator of the smog analysis application 330 of the cellular network 102 or a third-party vendor maintaining operation of the smog analysis application 330 located on an external server may input such information. In another embodiment, one or more servers 318 of the core 316 automatically receive the information from Web services via the Internet 104. For example, the information may include data such as GPS-based coordinates that define boundaries 126 (FIG. 1) of the bounded land area 124 (FIG. 1).

In one embodiment, the bounded land area 124 may coincide with the coverage area 114, however in other embodiments the bounded land area 124 may cover a least a portion of the coverage area 114 and/or at least portions of other coverage areas. In one embodiment, the maintenance operator, third-party vendor and/or the server 318 determines the bounded land area based upon results of past smog analysis by the smog analysis application 330, and/or based upon data corresponding to current or forecasted environmental conditions and/or other situational data (e.g., forest fires, weather (temperature, wind, humidity, etc.), time of day, time of year, traffic patterns). For example, based upon current weather conditions, traffic patterns and a forest fire located in a specific region within a coverage area, operators of the system wish to concentrate the computing resources to determine the smog status/prediction for the specific region within a short turn-around time.

In one embodiment, once a geographical bounded land area is determined, such as the bounded land area 124, the smog analysis application 330 generates and sends a data collection signal that includes geographic data defining the boundaries 126 of the bounded area of land 124. As described above, the data collection signal may also include instructions or commands that trigger or instruct the vehicle control systems 118 to collect sensor data or data from the memory 204. Upon receiving the data collection signal, each vehicle of the one or more vehicles 106 compares its current GPS coordinates obtained, for example, from a location sensor 120 sensor, with the received geographic data for determining if the vehicle is within the bounded land area 124. In one embodiment, if the vehicle determines that is located within the bounded land area, such as vehicle 106A, then the vehicle control system 118 collects data from the sensors 120 and/or the memory 204. However, if the vehicle determines that it is located outside the bounded land area, 124, such as vehicle 106C, then the vehicle control system 118 does not collect data from the sensors 120 and/or the memory 204. In one embodiment, the vehicle control system 118 is configured to override the triggering of the collection of data upon receipt of the data control signal if the vehicle control system 118 determines it is located outside of the bounded land area 124.

Accordingly, the core 316 receives data only from the subset of vehicles (i.e., 106A, 106B) of the one or more vehicles 106A, 106B, 106C that are located within the bounded area of land 124. In this manner, the smog analysis application 330 receives and processes only the data from vehicles located from within the predefined bounded land area 124 for determining the smog status/prediction for the predefined bounded land area 124, even though the data collection signal may be received by vehicles located outside the predefined bounded land area 124 but within the coverage area 114 of the base station 108A.

In an alternate embodiment, the smog analysis application 330 may receive (via the core 316) GPS information from the one or more vehicles 106 within the coverage area 114, compare the received GPS information to the coordinates associated with the bounded area of land, such as bounded area 124, and determine a subset of the one or more vehicles 106 located within the bounded area of land 124. The smog analysis application 330 may then generate and send a data collection signal only to the subset of the one or more vehicles (i.e. vehicles 106A and 106B) that are located in the bounded land area 124.

In another embodiment of the present disclosure, the core 316 is configured to send the results of the execution of the smog analysis application 330, referred to as traffic information, to a plurality of vehicles via at least one base station (e.g., the base station 108A). In one embodiment, the traffic information includes the determined smog status and/or the determined smog forecast. In another embodiment, the traffic data may also include alternate routes and smog statuses and smog forecasts for other base station coverage areas or other bounded land areas. In one embodiment, the smog analysis application is configured to access, upon execution by the core 316, external Web navigation services for determining alternate routes for any of the vehicles within coverage areas or bounded land areas for which a smog analysis has been performed. The determination of alternate routes may be based upon current locations and final destinations of the vehicles, which may be sent to the core 316 as a part of the data collected by the vehicles.

In a further embodiment, the core 316 is configured to send the traffic information to the plurality of vehicles via the base station 108A and one or more additional base stations 108B, 108C having different coverage areas. In this manner, a vehicle outside of one of the bounded land areas for which a smog analysis has been performed may use the traffic information to avoid any smoggy areas and choose an alternate route.

Figure 4:
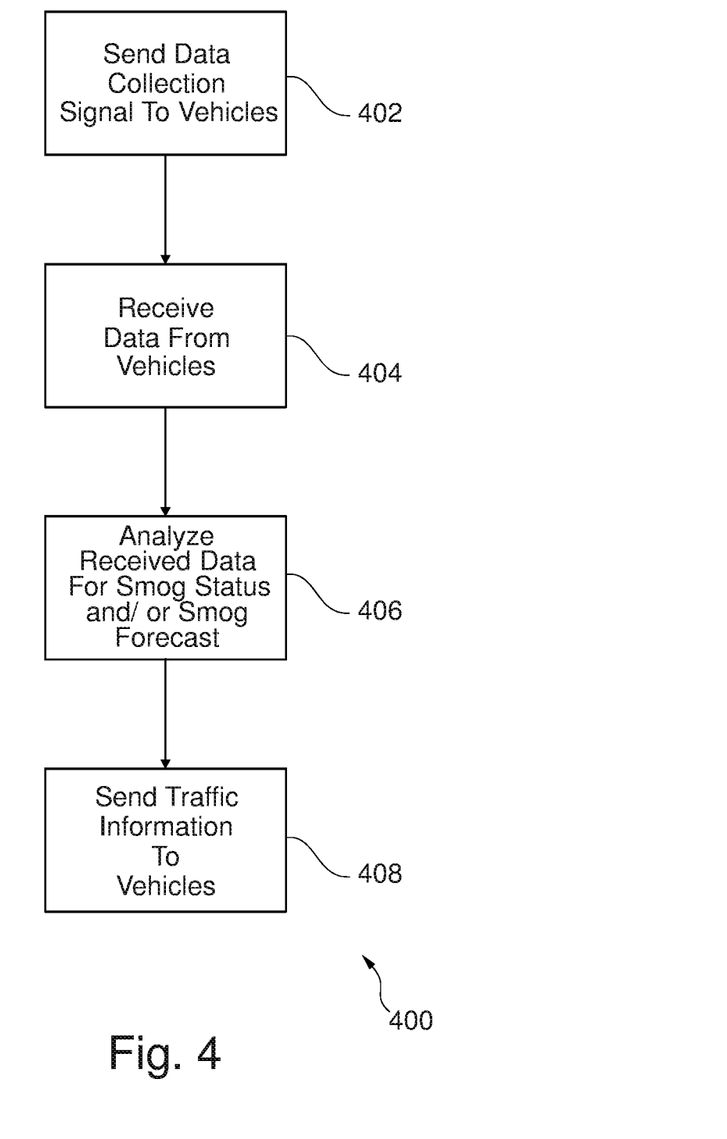
FIG. 4 is a flowchart for smog analysis, according to an embodiment of the present disclosure.

FIG. 4 is a flowchart 400 of the computer-implemented method for smog analysis, according to an embodiment of the present disclosure.

In step 402, a data collection signal is sent, by a cellular network using the smog analysis application, to one or more vehicles via a base station, wherein each vehicle includes one or more sensors. In one embodiment, the data collection signal is sent by the cellular network 102 via the base station 108A to one or more vehicles 106. In another embodiment, the data collection signal is sent by the core 110 of the cellular network 102 via the base station 108A and the wireless communications 116 to one or more vehicles 106.

In step 404, data is received, by the cellular network using the smog analysis application, from the one or more vehicles. In one embodiment, the data is received by the core 110 of the cellular network 102 via the base station 108A and the wireless communications 116. In another embodiment, the data is received by at least one server 318 of the core 316 of the cellular network 102 via the base station 108A and the fixed access network 112. The data includes sensor data collected by the one or more sensors 120 of the one or more vehicles 106 and/or data retrieved from a memory 204 of a vehicle control system 118 of the one or more vehicles 106. External data may also be received from sources external to the cellular network, including Web-based Internet sites and other external databases.

In step 406, the received data is analyzed, by a smog analysis application running either on the cellular network platform or on a server external to the platform, but communicatively coupled to the platform, to determine a smog status and/or a smog forecast. In one embodiment, the received data is analyzed by the smog analysis application 330 running on a platform of the cellular network 102, for example, distributed for execution across one or more servers 318 of the core 316 of the cellular network 102 via one or more of the physical infrastructure 302, the logical infrastructure 304, the software network functions infrastructure 306, the service orchestration infrastructure 308 and the management and orchestration layer 310 of the cellular network 102.

In step 408, traffic information is sent, by the cellular network, to a plurality of vehicles. In one embodiment, the core 316 of the cellular network 102 sends the traffic information to the plurality of vehicles 106 via the base station 108A and one or more additional base stations 108B, 108C having different coverage areas. The traffic information may include the determined smog status/smog forecast.

Figure 5:
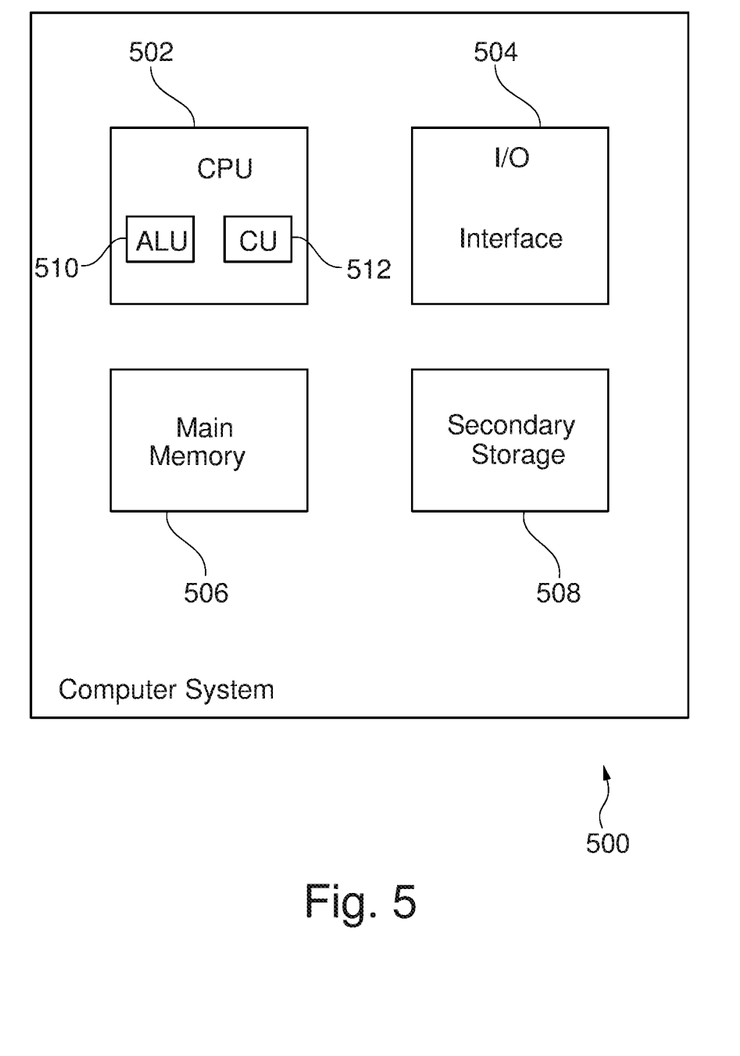
FIG. 5 is a schematic diagram of a computer system, according to an embodiment of the present disclosure.

FIG. 5 illustrates a computer system 500, according to an embodiment of the present disclosure. The computer system 500 may represent embodiments of the server 318 (FIG. 3) and the vehicle control unit (FIG. 2), although the scope of the present disclosure is not limited to, and may not include, each component of the computer system 500. General purpose computer systems are well known in the art, and thus the computer system 500 may include any other components known in the state of the art, and functioning and interacting with each other in such means known, even if not explicitly illustrated.

The computer system 500 includes, but is not limited to, a central processing unit (CPU) 502, an input/output interface 504, main memory 506 and secondary storage 508. The CPU 502 may be a microprocessor chip. The CPU 502 controls the activities of any other chips of the computer system 500 as well as any outside devices connected to the computer system 500 via the I/O interface 504, such as display devices, printers, touch screens and keypads. In addition, the CPU 502 performs logical and computational tasks, for example execution of any program or software code stored in the secondary storage 508 (e.g., a hard drive or solid state drive), portions of which are received by the main memory 506 (e.g., random access memory or any other volatile memory) for execution.

The CPU 502 may also include an arithmetic logical unit (ALU) 510 for processing data after data is stored in main memory 506, including operations of addition, subtraction, multiplication, division, logic and comparison, and a control unit (CU) 512 for selecting operations, instructions and/or checking sequence in which instructions are executed.

Although not illustrated, the computer system 500 includes data buses, address buses and control buses that facilitate access to and communication of information, such as data and instructions.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for smog analysis, the computer-implemented method comprising:
    sending, by one or more computer processors, a data collection signal to one or more vehicles via a base station, wherein each vehicle includes one or more sensors;
    receiving, by one or more computer processors, data from the one or more vehicles at a determined frequency based on a previously received data, the data including sensor data collected by the one or more sensors of the one or more vehicles, wherein the data received from a vehicle of the one or more vehicles is selected from the group consisting of one or more of outside temperature, speed of the vehicle, revolutions per second of an engine of the vehicle, oil temperature of the engine, water temperature of the engine, emissions data, weight of the vehicle, location of the vehicle, audio data from a user of the vehicle, engine-maintenance history, accident history of the vehicle, pollution-under-control (PUC) data and vehicle-to-vehicle (V2V) network data;
    analyzing, by one or more computer processors, the received data for determining a smog status; and
    sending, by one or more computer processors, traffic information to a plurality of vehicles, the traffic information including the determined smog status, the plurality of vehicles including the one or more vehicles.

2. The computer-implemented method of claim 1, further comprising:
    defining, by one or more computer processors, a bounded area of land, wherein a coverage area of the base station includes at least a portion of the bounded area of land, wherein the data collection signal includes geographic data defining boundaries of the bounded area of land, and wherein
    receiving, by one or more computer processors, the data from the one or more vehicles comprises receiving, by one or more computer processors, data only from a subset of the one or more vehicles located within the bounded area of land.

3. The computer-implemented method of claim 2, further comprising:

upon receiving the data collection signal, each vehicle of the one or more vehicles compares current GPS coordinates obtained from a sensor with the received geographic data for determining if the vehicle is within the bounded land area; and a vehicle collects data by the one or more sensors if the vehicle is determined to be within the bounded land area.

4. The computer-implemented method of claim 1, further comprising:

triggering, by one or more computer processors, upon receipt of the data collection signal, the one or more sensors of the one or more vehicles to collect the sensor data.

5. The computer-implemented method of claim 4, wherein the one or more sensors is selected from the group consisting of audio sensors, visual sensors, temperature sensors, engine-based sensors, emission sensors and GPS sensors.

6. The computer-implemented method of claim 1, wherein determining, by one or more computer processors, the frequency of sending the data collection signal is further based on the determined smog status.

7. The computer-implemented method of claim 1, further comprising receiving, by one or more computer processors, external data from internet services and/or databases, the external data selected from the group consisting of weather data, weight of the one or more vehicle, engine-maintenance history of the one or more vehicles, accident history of the one or more vehicles, pollution-under-control (PUC) data of the one or more vehicles, and wherein analyzing the received data for determining a smog status comprises analyzing the received data from the one or more vehicles and the received external data for determining the smog status.

8. The computer-implemented method of claim 1, wherein the smog status is determined for a predefined bounded area of land, wherein a coverage area of the base station includes at least a portion of the bounded area of land, and wherein the traffic information is selected from the group consisting of alternative route information, smog status of other predefined bounded areas of land and smog status forecasts for the predefined bounded area of land and the other predefined bounded areas of land.

9. The computer-implemented method of claim 8, wherein sending, by one or more computer processors, the traffic information to the plurality of vehicles comprises sending, by one or more computer processors, the traffic information to the plurality of vehicles via one or more additional base stations, the one or more additional base stations having different coverage areas from one another and from the coverage area of the base station.

10. A computer program product for smog analysis, the computer program product comprising:

one or more computer readable storage media; and program instructions stored on the one or more computer readable storage media, the program instructions comprising:

program instructions to send a data collection signal to one or more vehicles via a base station, wherein each vehicle includes one or more sensors;

program instructions to receive data from the one or more vehicles at a determined frequency based on a previously received data, the data including sensor data collected by the one or more sensors of the one or more vehicles, wherein the data received from a vehicle of the one or more vehicles is selected from the group consisting of one or more of outside temperature, speed of the vehicle, revolutions per second of an engine of the vehicle, oil temperature of the engine, water temperature of the engine, emissions data, weight of the vehicle, location of the vehicle, audio data from a user of the vehicle, engine-maintenance history, accident history of the vehicle, pollution-under-control (PUC) data and vehicle-to-vehicle (V2V) network data;

program instructions to analyze the received data for determining a smog status; and program instructions to send traffic information to a plurality of vehicles, the traffic information including the determined smog status, the plurality of vehicles including the one or more vehicles.

11. The computer program product of claim 10, further comprising program instructions stored on the one or more computer readable storage media, to:

define a bounded area of land, wherein a coverage area of the base station includes at least a portion of the bounded area of land, wherein the data collection signal includes geographic data defining boundaries of the bounded area of land, and wherein receive the data from the one or more vehicles comprises receiving, by one or more computer processors, data only from a subset of the one or more vehicles located within the bounded area of land.

12. The computer program product of claim 11, further comprising program instructions stored on the one or more computer readable storage media, to:

upon receiving the data collection signal, each vehicle of the one or more vehicles compares current GPS coordinates obtained from a sensor with the received geographic data for determining if the vehicle is within the bounded land area; and a vehicle collects data by the one or more sensors if the vehicle is determined to be within the bounded land area.

13. The computer program product of claim 10, further comprising program instructions stored on the one or more computer readable storage media, to:

trigger upon receipt of the data collection signal, the one or more sensors of the one or more vehicles to collect the sensor data.

14. The computer program product of claim 13, wherein the one or more sensors is selected from the group consisting of audio sensors, visual sensors, temperature sensors, engine-based sensors, emission sensors and GPS sensors.

15. A computer system for smog analysis, the computer system comprising:

one or more computer processors;

one or more computer readable storage media; and program instructions, stored on the one or more computer readable storage media for execution by at least one of the one or more computer processors, the program instructions comprising:

program instructions to send a data collection signal to one or more vehicles via a base station, wherein each vehicle includes one or more sensors;

program instructions to receive data from the one or more vehicles at a determined frequency based on a previously received data, the data including sensor data collected by the one or more sensors of the one or more vehicles, wherein the data received from a vehicle of the one or more vehicles is selected from the group consisting of one or more of outside temperature, speed of the vehicle, revolutions per second of an engine of the vehicle, oil temperature of the engine, water temperature of the engine, emissions data, weight of the vehicle, location of the vehicle, audio data from a user of the vehicle, engine-maintenance history, accident history of the vehicle, pollution-under-control (PUC) data and vehicle-to-vehicle (V2V) network data;

program instructions to analyze the received data for determining a smog status; and program instructions to send traffic information to a plurality of vehicles, the traffic information including the determined smog status, the plurality of vehicles including the one or more vehicles.

16. The computer system of claim 15, further comprising program instructions stored on the one or more computer readable storage media for execution by at least one of the one or more computer processors, to:

define a bounded area of land, wherein a coverage area of the base station includes at least a portion of the bounded area of land, wherein the data collection signal includes geographic data defining boundaries of the bounded area of land, and wherein receive the data from the one or more vehicles comprises receiving, by one or more computer processors, data only from a subset of the one or more vehicles located within the bounded area of land.

17. The computer system of claim 16, further comprising program instructions stored on the one or more computer readable storage media for execution by at least one of the one or more computer processors, to:

upon receiving the data collection signal, each vehicle of the one or more vehicles compares current GPS coordinates obtained from a sensor with the received geographic data for determining if the vehicle is within the bounded land area; and a vehicle collects data by the one or more sensors if the vehicle is determined to be within the bounded land area.

18. The computer system of claim 15, further comprising program instructions stored on the one or more computer readable storage media for execution by at least one of the one or more computer processors, to:

trigger upon receipt of the data collection signal, the one or more sensors of the one or more vehicles to collect the sensor data.

19. The computer system of claim 18, wherein the one or more sensors is selected from the group consisting of audio sensors, visual sensors, temperature sensors, engine-based sensors, emission sensors and GPS sensors.

20. A 5G cellular network configured to:

send a data collection signal to one or more vehicles via a base station, wherein each vehicle includes one or more sensors;

receive data from the one or more vehicles, the data including sensor data collected by the one or more sensors of the one or more vehicles at a determined frequency based on a previously received data, wherein the data received from a vehicle of the one or more vehicles is selected from the group consisting of one or more of outside temperature, speed of the vehicle, revolutions per second of an engine of the vehicle, oil temperature of the engine, water temperature of the engine, emissions data, weight of the vehicle, location of the vehicle, audio data from a user of the vehicle, engine-maintenance history, accident history of the vehicle, pollution-under-control (PUC) data and vehicle-to-vehicle (V2V) network data;

analyze the received data for determining a smog status; and send traffic information to a plurality of vehicles, the traffic information including the determined smog status, the plurality of vehicles including the one or more vehicles.

* * * * *